(12) United States Patent  
Foo et al.

(10) Patent No.: US 10,921,395 B2  
(45) Date of Patent: Feb. 16, 2021

(54) IMAGE-GUIDED BIOPSY TECHNIQUES

(71) Applicants: GE Precision Healthcare LLC, Wauwatosa, WI (US); Wisconsin Alumni Research Foundation, Madison, WI (US)

(72) Inventors: Thomas Kwok-Fah Foo, Clifton Park, NY (US); Jhimli Mitra, Niskayuna, NY (US); Bo Wang, Schenectady, NY (US); Lowell Scott Smith, Niskayuna, NY (US); David Martin Mills, Niskayuna, NY (US); Warren Lee, Niskayuna, NY (US); James Hartman Holmes, Cross Plains, WI (US); Bryan Bednarz, Madison, WI (US); Roberta Marie Strigel, Madison, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 448 days.

(21) Appl. No.: 15/870,519

(22) Filed: Jan. 12, 2018

(65) Prior Publication Data

US 2019/0219647 A1    Jul. 18, 2019

(51) Int. Cl.
*G01R 33/00*  (2006.01)
*G01R 33/28*  (2006.01)
(Continued)

(52) U.S. Cl.
CPC ............ *G01R 33/285* (2013.01); *A61B 5/055* (2013.01); *A61B 8/0841* (2013.01);
(Continued)

(58) Field of Classification Search
CPC ..... A61B 8/526; A61B 8/4416; A61B 8/5261; A61B 5/055; A61B 8/461; A61B 8/0841;
(Continued)

(56) References Cited

U.S. PATENT DOCUMENTS 6,889,073 B2    5/2005    Lampman et al.
6,937,883 B2    8/2005    Prince
(Continued)

FOREIGN PATENT DOCUMENTS

WO    2012032308 A1    3/2012

OTHER PUBLICATIONS

U.S. Appl. No. 62/477,294, filed Mar. 27, 2017, Warren Lee.
(Continued)

*Primary Examiner* — Joel Lamprecht
(74) *Attorney, Agent, or Firm* — Armstrong Teasdale LLP

(57) ABSTRACT

A system and method for providing virtual real-time MRI-guidance for a biopsy outside of a conventional MRI scanner is described. MR images and ultrasound images of a region of a patient's body are simultaneously acquired during a pre-biopsy procedure. Respiratory states that the patient may experience during the biopsy are then determined from the acquired ultrasound images, and each respiratory state is associated with corresponding MR images. The MR images are indexed with their corresponding respiratory state. Ultrasound images are then acquired of the patient during a biopsy procedure. The respiratory state of the patient is determined from the ultrasound images, and the corresponding indexed MR images are displayed.

20 Claims, 5 Drawing Sheets

(51) Int. Cl.

| | | |
|---|---|---|
| *A61B 8/08* | (2006.01) | |
| *A61B 8/00* | (2006.01) | |
| *A61B 5/055* | (2006.01) | |
| *A61B 6/00* | (2006.01) | |
| *A61B 90/00* | (2016.01) | |
| *A61B 10/02* | (2006.01) | |
| *A61B 17/34* | (2006.01) | |

(52) U.S. Cl.
CPC ............ *A61B 8/4416* (2013.01); *A61B 8/461* (2013.01); *A61B 8/5261* (2013.01); *A61B 8/5276* (2013.01); *A61B 6/502* (2013.01); *A61B 8/5269* (2013.01); *A61B 10/0233* (2013.01); *A61B 2017/3413* (2013.01); *A61B 2090/374* (2016.02); *A61B 2090/378* (2016.02)

(58) Field of Classification Search
CPC ...... A61B 2017/3413; A61B 2090/374; A61B 8/5269; A61B 6/502; A61B 2090/378; A61B 10/0233; A61B 5/7289; A61B 5/0035; A61B 3/4814; A61B 3/5673; G01R 33/285; G01R 33/4814; G01R 33/5673

See application file for complete search history.

(56) References Cited

U.S. PATENT DOCUMENTS

| | | | |
|---|---|---|---|
| 8,155,729 | B1 | 4/2012 | Hsieh et al. |
| 9,014,784 | B2 | 4/2015 | Yang et al. |
| 9,554,779 | B2 | 1/2017 | Larson et al. |
| 9,636,072 | B2 | 5/2017 | Shores et al. |
| 2004/0267121 | A1 | 12/2004 | Sarvazyan et al. |
| 2006/0184003 | A1* | 8/2006 | Lewin ....................... G06T 7/73 600/414 |
| 2012/0143029 | A1* | 6/2012 | Silverstein ........... A61B 5/7475 600/374 |
| 2014/0275962 | A1 | 9/2014 | Foo et al. |
| 2015/0201910 | A1* | 7/2015 | Zhao ........................ G06T 7/33 600/424 |
| 2016/0278746 | A1* | 9/2016 | Hancu ................ A61B 10/0266 |

OTHER PUBLICATIONS

Piron, C.A., et al.; "A Hybrid Breast Biopsy System Combining Ultrasound and MRI", IEEE Transactions on Medical Imaging, vol. 22, Issue 09, pp. 1100-1110, Sep. 2003.

Liberman, Laura, et al.; "MRI-guided 9-gauge vacuum-assisted breast biopsy: initial clinical experience.", AJR, American Journal of Roentgenology, vol. 185, Issue 01, pp. 183-193, Jul. 2005.

Van den Bosch, M.A.A.J., et al.; "MRI-Guided Needle Localization of Suspicious Breast Lesions: Results of a Freehand Technique", European Radiology, vol. 16, Issue 08, pp. 1811-1817, Aug. 2006.

Tang, Annie M., et al.; "Simultaneous Ultrasound and MRI System for Breast Biopsy: Compatibility Assessment and Demonstration in a Dual Modality Phantom", IEEE Transactions on Medical Imaging, vol. 27, Issue 02, pp. 247-254, Feb. 2008.

Smith, Matthew, et al.; "A novel MR-guided interventional device for 3D circumferential access to breast tissue.", Medical Physics, vol. 35, Issue 08, pp. 3779-3786, Aug. 2008.

Han, Boo-Kyung, et al.; "Outcome of MRI-Guided Breast Biopsy.", AJR, American Journal of Roentgenology, vol. 191, Issue 06, pp. 1798-1804, Dec. 2008.

Liang, Kaicheng, et al.; "3D Ultrasound Guidance of Autonomous Robotic Breast Biopsy: Feasibility Study", Ultrasound Med Biol., vol. 36, Issue 01, pp. 173-177, Jan. 2010.

Siegler, Peter, et al.; "Supine breast MRI.", Journal of Magnetic Resonance Imaging, vol. 34, Issue 05, pp. 1212-1217, Nov. 2011.

El Khouli, Riham H., et al.; "The effects of applying breast compression in dynamic contrast material-enhanced MR imaging.", Radiology, pp. 79-90, Jul. 2014.

Vasanawala, Shreyas S., et al.; "Development and Clinical Implementation of Next Generation Very Light Weight and Extremely Flexible Receiver Arrays for Pediatric MRI", Medical Physics, Apr. 29, 2017.

Bednarz, B., et al.; Presentation "A Hands-Free MR-Compatible Volumetric Ultrasound Probe for Real-Time Motion Management During External Beam Radiotherapy", Jul. 31, 2017.

Lee, Warren, et al.; "A Magnetic Resonance E4D Ultrasound Probe for Motion Management of Radiation Therapy," 2017 IEEE International Ultrasonics Symposium (IUS), Washington, DC, 2017, pp. 1-4.

\* cited by examiner

IMAGE-GUIDED BIOPSY TECHNIQUES

STATEMENT REGARDING FEDERALLY SPONSORED RESEARCH & DEVELOPMENT

This invention was made with Government support under contract number R01CA190928 awarded by the National Cancer Institute of the National Institutes of Health. The Government has certain rights in the invention.

CROSS-REFERENCE TO RELATED APPLICATIONS

This invention was made with government support under CA190298 awarded by the National Institutes of Health. The government has certain rights in the invention.

BACKGROUND

The subject matter disclosed herein relates to the use of ultrasound and magnetic resonance imaging modalities, such as for use during image-guided breast biopsies.

An image-guided breast biopsy typically involves using an imaging procedure, such as ultrasound imaging or magnetic resonance imaging (MRI), to guide the biopsy needle to extract tissue at a suspect lesion in a patient's body. Ultrasound imaging provides a high frame rate to follow the trajectory of the needle during the biopsy process. However, conventional ultrasound imaging has a limited field of view, which can lead to misinterpretations in the position of the suspect lesion or the needle. In contrast, MRI provides a higher sensitivity in the detection of lesions. It also delivers three-dimensional positional information and a large field of view. A typical MRI-guided breast biopsy places the patient in the prone position with the breast of the patient immobilized by two compression plates and a grid. The grid is used to locate the suspect lesion and indicate the insertion point of the biopsy needle. Due to limited patient access within the MRI scanner, the patient must be periodically removed from the MRI to reposition the biopsy needle and moved back into the MRI scanner for further imaging. Thus, active visualization of the progression of the biopsy needle or verification of the biopsy site cannot be performed while the patient is outside the MRI scanner. Additionally, breast compression can be very painful for the patient and can contribute to mischaracterization of a lesion type or underestimation of the size of the lesion. Unlike, MRI-guided breast biopsies, ultrasound-guided breast biopsies place the patient in a supine position and do not require breast compression.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a method for providing real-time image guidance for a biopsy includes acquiring magnetic resonance (MR) images and pre-biopsy ultrasound images of an anatomical region of a patient. The MR images and the pre-biopsy ultrasound images are acquired simultaneously over a period of time. The method includes determining respiratory states of the patient from the pre-biopsy ultrasound images. A respiratory state is associated with each of the MR images or each of a set of MR images. The method also includes indexing the MR images with their corresponding respiratory state and storing the MR images or each of a set of MR images with their corresponding respective respiratory state.

In another embodiment, a method for providing real-time image guidance for a biopsy includes acquiring biopsy ultrasound images of an anatomical region of a patient, and determining a biopsy respiratory state from the biopsy ultrasound images. The biopsy respiratory state is identified as a respiratory state of the patient associated with one or more stored MR images of the patient. The method includes retrieving the stored MR images that correspond to the identified respiratory state, and displaying the stored MR images that correspond to the identified respiratory state.

In another embodiment, an interventional guidance system includes an ultrasound imaging system configured to acquire pre-biopsy ultrasound images and biopsy ultrasound images of an anatomical region of a patient, and a processor. The processor is configured to determine one or more respiratory states of the patient from the acquired pre-biopsy ultrasound images, associate the one or more respiratory states with each MR image, index the MR images with their associated respiratory states, and determine a biopsy respiratory state from the biopsy ultrasound images. The biopsy respiratory state is identified as corresponding to one of the respiratory states determined from the pre-biopsy ultrasound images. This in turn determines the MR images or the set of MR images acquired from the pre-biopsy scan that correspond to the current respiratory state. Thus, an accurate representation of the location of the anatomical structure at that point in time can be presented or displayed to guide the biopsy procedure, specifically the biopsy needle trajectory to the biopsy target. The processor is also configured to display the MR images that correspond to the identified respiratory state.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
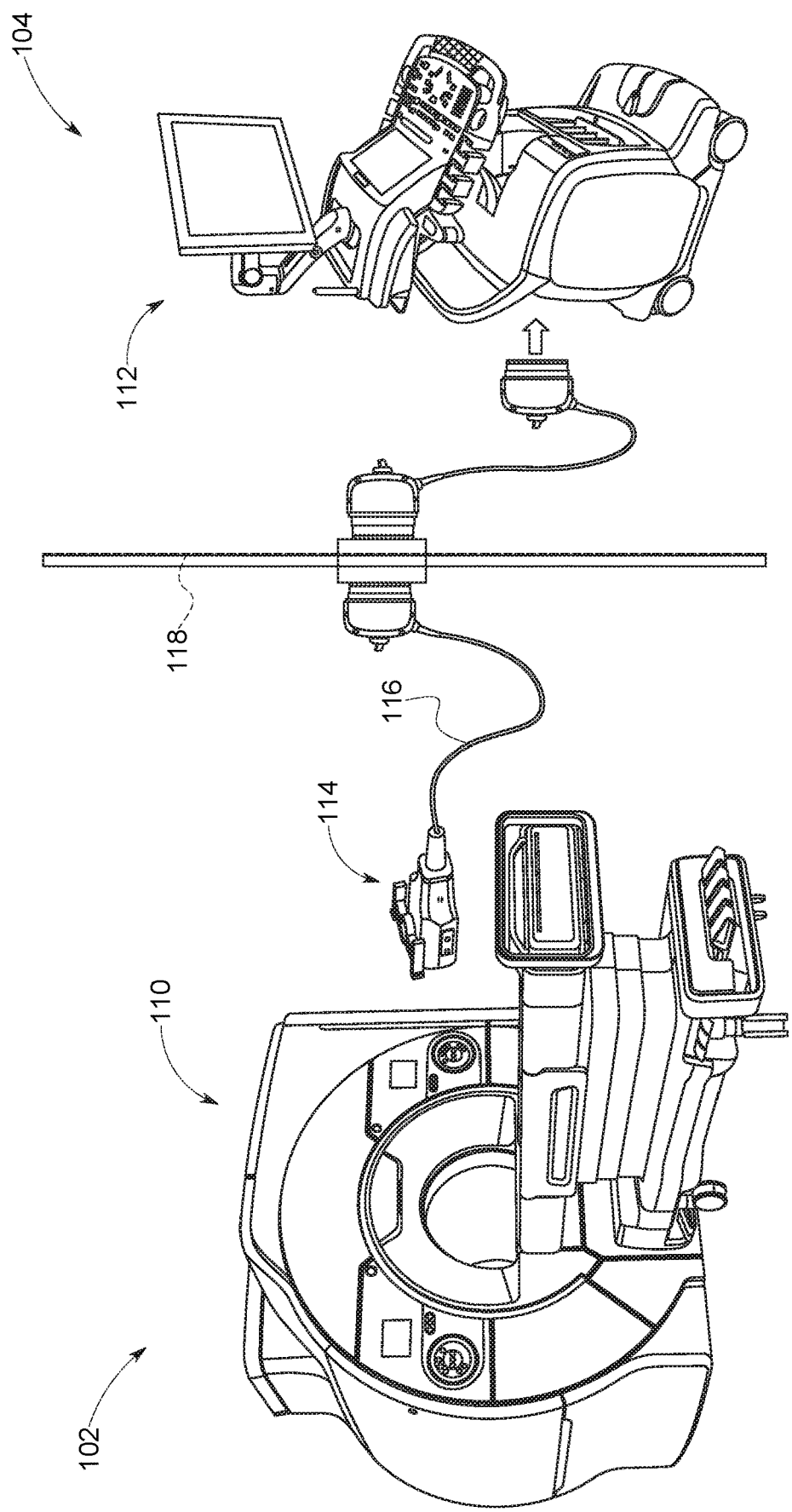
FIG. 1 illustrates an embodiment of a combined magnetic resonance and ultrasound imaging system with a MR-compatible, real-time, three-dimensional imaging ultrasound probe, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, the term "virtual real-time magnetic resonance image(s)" refers to the display of previously acquired MR images that correspond to a current respiratory state of a patient (as further explained below). Thus, displaying these MR images provides "real-time" MR imaging of the patient even though the current image modality being employed is ultrasound. By displaying the correct previously acquired MR images or set of MR images that accurately represents the positions of the anatomical structures within the imaging field-of-view, a system and process is described that enables "real-time" MR imaging when another imaging modality, such as ultrasound, is employed.

The present approach relates to using virtual real-time magnetic resonance images for direct imaging guidance of a biopsy procedure. In certain implementations discussed herein, the imaging and biopsy procedures are performed on a patient's breast without breast compression or the use of plates to guide the biopsy needle. Although certain aspects of the present disclosure focus on imaging guidance of breast biopsy procedures, a person of ordinary skill in the art should recognize that the present approach can be applied to other suitable regions of a person's body. The image-guided biopsy procedure combines MR imaging with real-time ultrasound imaging to provide guidance for a biopsy needle. During the pre-biopsy stage of a breast biopsy procedure, an ultrasound probe acquires ultrasound images of the breast of a patient simultaneously with the acquisition of MR images in a MR scanner. The ultrasound probe is MR-compatible such that it is able to operate simultaneously in an MR scanner while the MR scanner is in operation. The ultrasound images provide a measure of the patient's respiratory state. Concurrently acquired MR images are then indexed (e.g., stored in a table) with the determined respiratory state of the patient such that each respiratory state determined from the ultrasound images has a corresponding MR image. The ultrasound images also help determine a mathematical transformation function that can be used to deform the acquired MR images to represent the real-time spatial disposition of the breast of the patient in a subsequent biopsy procedure. During the biopsy stage of the breast biopsy procedure, the ultrasound probe acquires ultrasound images of the breast of the patient in real time. The ultrasound images are used to identify the current respiratory state of the patient. A processor then accesses the stored, pre-acquired MR images from the pre-biopsy stage that are associated with different respiratory states. The processor then identifies the respiratory state which may be represented by one or more identifiers from a set of identifiers. The identifiers may consist of a set of one or more numbers or parameters that are linked to a unique respiratory state. The processor then searches for the corresponding indexed pre-biopsy MR images or set of images that match the current respiratory state, and the images are displayed to guide the biopsy needle.

FIG. 1 shows a possible configuration of the MRI system 110 and ultrasound system 112 suitable for concurrent image acquisition. An MR-compatible probe 114 for use with the MRI system 110 is connected to the ultrasound system 112 in a separate ultrasound control room 104 via a probe cable 116 that passes through the shielded wall 118 of the MRI room 102. The probe cable 116 does not significantly degrade the image quality of the ultrasound system 112 due to the presence of transmitters and low noise amplifiers in the probe handle. The probe components are chosen to have very low or no ferromagnetic material content for MR compatibility. Additionally, the probe 114 is designed to minimize loops in electronic circuitry to avoid induced currents in the changing magnetic field. The entirety of the probe 114, including the transducer face, housing, and cable 116, is enclosed in a full electromagnetic interference (EMI) shield to prevent unwanted ultrasound-MRI interference. The transducer face may be covered, for example, by a 10 to 15 micron thick aluminum foil, to electrically shield the transducer while having a negligible impact on acoustic performance.

In another possible configuration of the MRI system 110 and ultrasound system 112, the MR-compatible probe 114 may be hands-free and electronically steerable. The probe 114 may be operated remotely from the control room 104 of the ultrasound system 112 or at another suitable location. The probe 114 also may be fixed to the breast of the patient via Velcro straps, in a rigid breast-constraining structure that allows biopsy needle access, or another suitable means to allow for simultaneous MR and ultrasound imaging.

Figure 2:
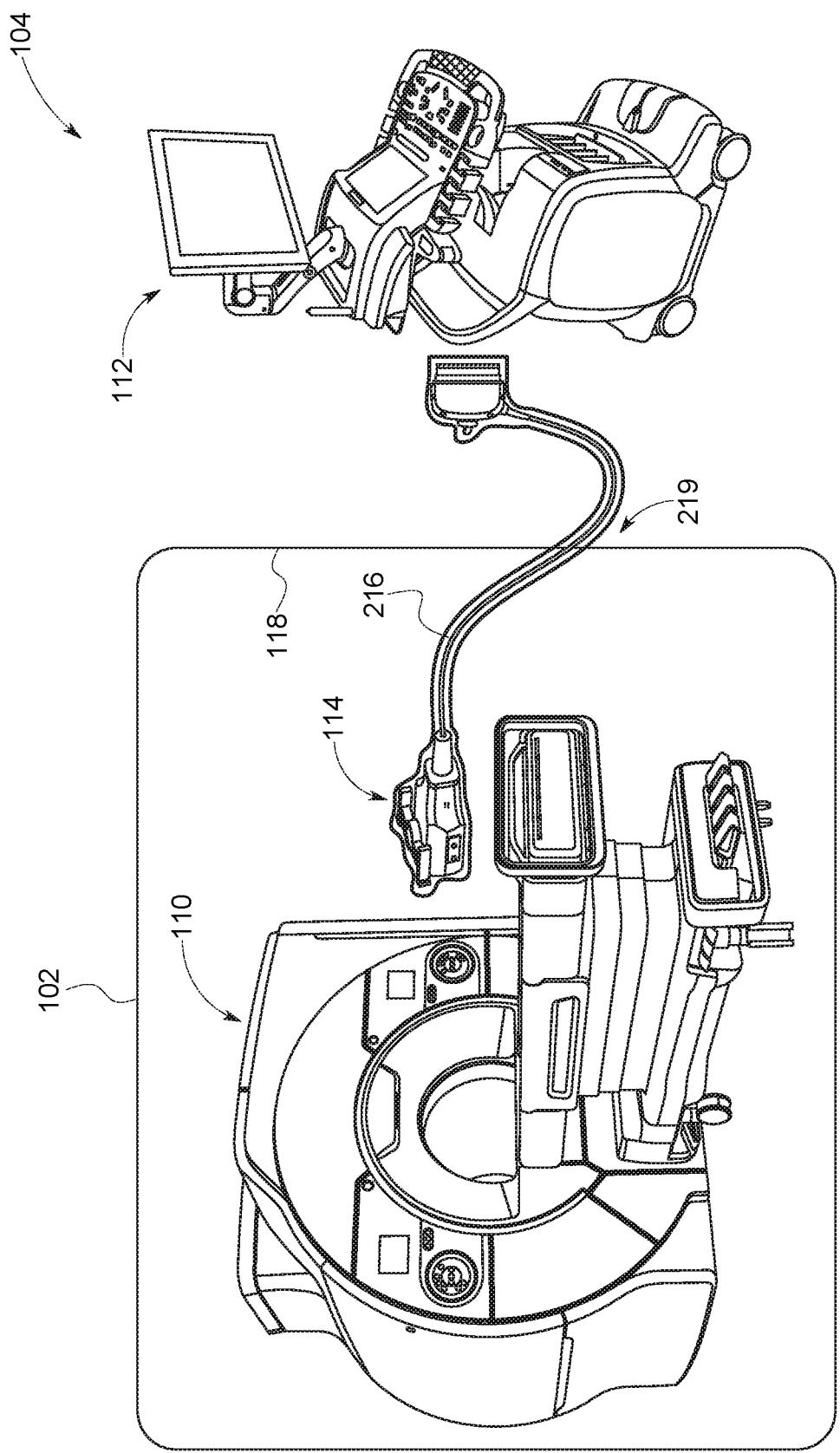
FIG. 2 illustrates an embodiment of an alternative combined magnetic resonance and ultrasound imaging system with a MR-compatible ultrasound probe having a single, continuous shield cable that plugs into the ultrasound system, in accordance with aspects of the present disclosure.

FIG. 2 illustrates another possible configuration of the MRI system 110 and ultrasound system 112. The MR-compatible probe 114 is attached to a single, continuous, shielded probe cable 216, which penetrates the wall separating the MR room 102 from the control room 104 or at another suitable location. The shielded probe cable 216 plugs into the ultrasound system 112 in the control room 104. The electrical shield of the shielded probe cable 216 may be connected to a shielded wall 118 of the MR room 102 at the penetration location 219 in order to provide full EMI shielding to reduce unwanted ultrasound-MRI interference.

Figure 3:
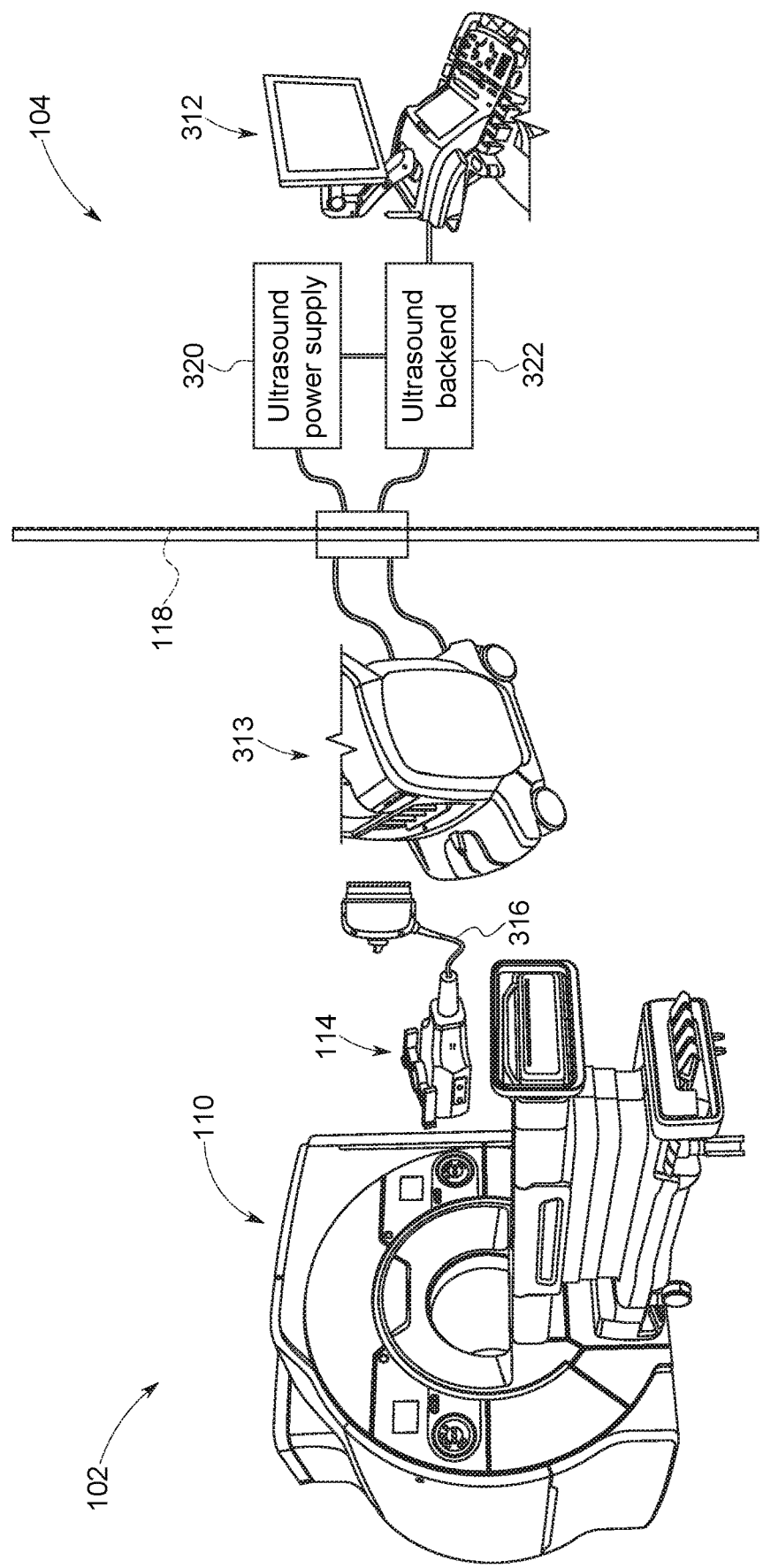
FIG. 3 illustrates an embodiment of an alternative combined magnetic resonance and split ultrasound imaging system arrangement, in accordance with aspects of the present disclosure.

FIG. 3 shows an alternative split ultrasound system arrangement suitable for concurrent MR and ultrasound image acquisition. The ultrasound system is split into an MR-compatible front end 313 which is placed in the MR room 102, and a power supply 320 and ultrasound backend 322 which are placed in the ultrasound control room 104. Power supply 320 and ultrasound backend 322 may be separate components or housed together in a single unit 312. Power and digital communication lines pass through the shielded wall 118 between the front end 313 and the power supply 320 and backend 322. The advantage of this system arrangement is that since the ultrasound system has a MR-compatible front end 313, a shorter probe cable 316 (e.g., two meters to three meters) would be sufficient to connect the probe to the front end. For probes that do not have transmitters and low-noise amplifiers integrated in the probe handle, reducing the cable length reduces parasitic load and thus improves image quality.

Figure 4:
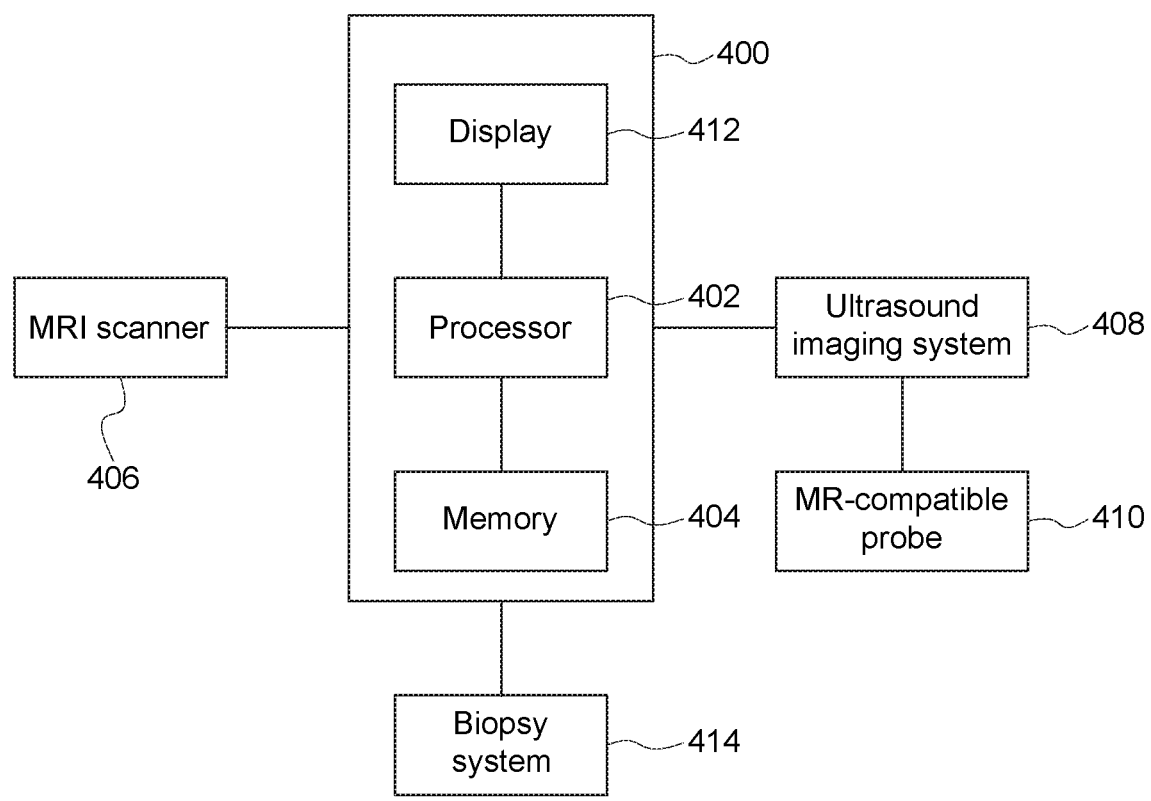
FIG. 4 illustrates an embodiment of an interventional guidance system, in accordance with aspects of the present disclosure.

FIG. 4 shows a high-level view of components of an interventional guidance system 400 that may be suitable in the implementation of the present approach. In particular, the present approach may be implemented as one or more executable routines stored on memory 404 or data storage components of the processor 402 of the interventional guidance system 400. The illustrated interventional guidance system 400 communicates with an MRI scanner 406 configured to acquire MR images of a patient during a pre-biopsy stage. The MRI scanner may be at any field strength. The interventional guidance system 400 also communicates with an ultrasound imaging system 408 configured to acquire ultrasound images of the patient with an MR-compatible probe 410 during the pre-biopsy stage and during a biopsy procedure. The processor 402 may be a component of a picture archival system, a dedicated navigational system (as shown in FIG. 4), or part of the ultrasound imaging system 408 where the ultrasound system 408 functions as or otherwise provides navigation functionality. The processor 402 may store the acquired images from the MRI scanner, the ultrasound imaging system, or both. The interventional guidance system 400 may also communicate with a biopsy system 414 to provide guidance during a biopsy procedure. We note that the system and process described entails two stages in the biopsy procedure, a pre-biopsy stage where simultaneous MR and ultrasound imaging occurs, and an actual biopsy stage or procedure where ultrasound imaging and needle insertion occurs.

Figure 5:
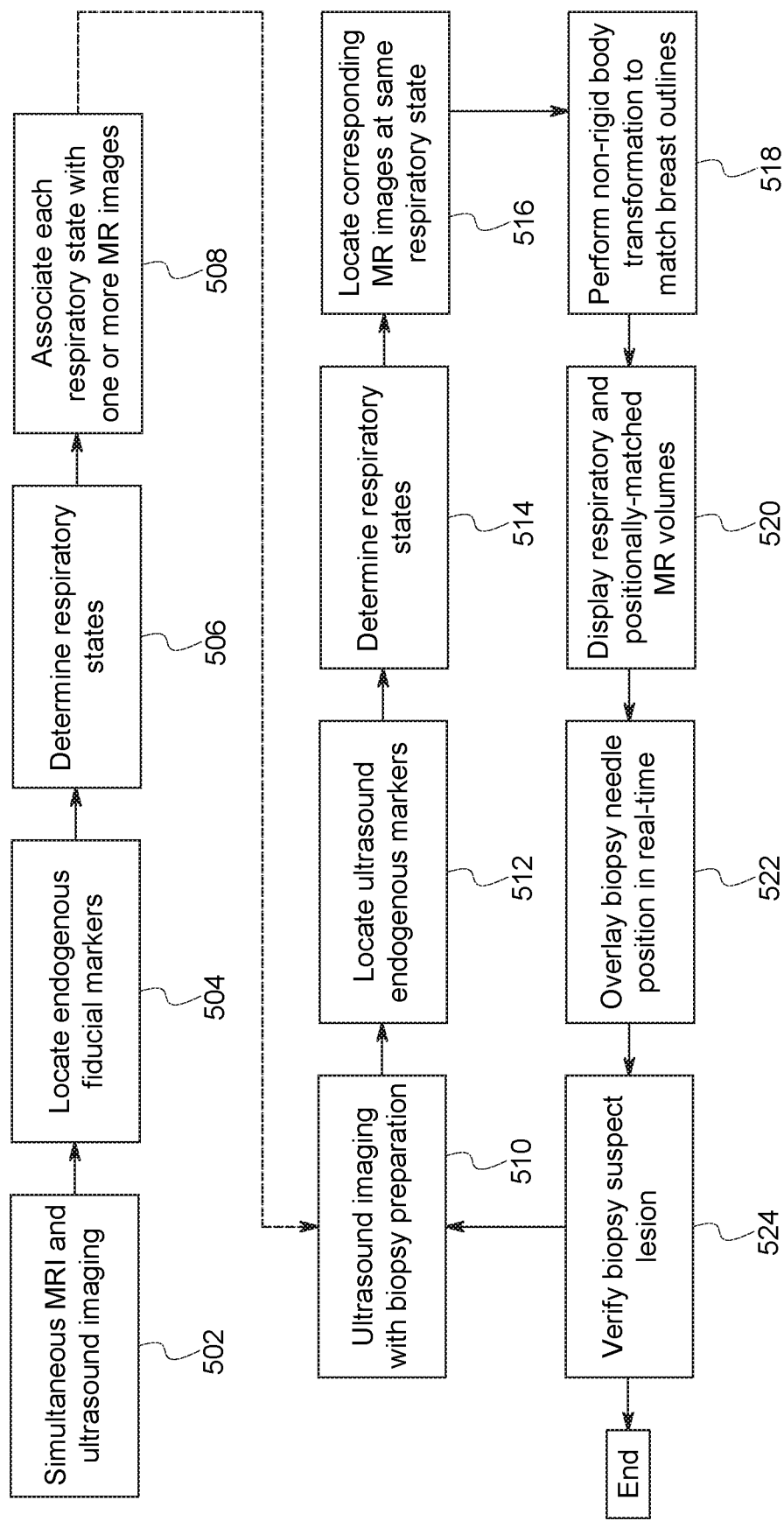
FIG. 5 illustrates a flowchart for an embodiment of a combined magnetic resonance and ultrasound image-guided biopsy, in accordance with aspects of the present disclosure.

FIG. 5 illustrates a flowchart of a method of providing virtual real-time magnetic resonance images for direct imaging guidance of a breast biopsy of a patient, such as a patient in the supine position. The method consists of two stages of imaging: (1) a pre-biopsy stage (i.e., steps 502 to 508); and (2) a biopsy stage (steps 510 to 524). The steps of the pre-biopsy stage may occur at any time before the biopsy stage and may occur at a different location or the same location. For example, the pre-biopsy stage may be conducted in the MR scanner and the biopsy procedure may be performed outside the MR scanner, such as in a standard clinical examination room.

During the pre-biopsy stage, in step 502, three-dimensional MR images and real-three-dimensional (four-dimensional) ultrasound images of a patient's breast are acquired simultaneously in time. The MR images and each ultrasound images do not have to be completely aligned in time. If the images are not temporally aligned, techniques, such as temporal interpolation, may be used to substantially align or substantially link the images. The MR images may be acquired without breast compression or with limited compression or positioning. For example, in one embodiment, the MR system uses a soft, conformable, multi-element, lightweight coil during acquisition of the MR images. In step 504, one or more endogenous fiducial markers are identified in the ultrasound images at each time frame. For example, the endogenous fiducial markers may include blood vessels, the structural anatomy of the breast (e.g., the chest wall), or the suspect lesion itself.

In step 506, respiratory states at each time frame of the ultrasound images are determined using positional or shape changes in the ultrasound images of the identified endogenous fiducial marker of step 504. The respiratory states represent the possible respiratory states the patient may experience during the biopsy procedure, for both the pre-biopsy and biopsy stages. For example, the respiratory states may include inhalation, exhalation, short-breath holds, irregular breaths, or any sub-state of a respiratory state. In step 508, each determined respiratory state or sub-state is then associated with one or more acquired MR images. A table or index of the determined respiratory states with their corresponding MR images is created.

During the biopsy stage, the ultrasound probe may be similar or identical to the ultrasound probe used to acquire ultrasound images during the pre-biopsy stage. In one embodiment, the ultrasound probe may be manually manipulated in the biopsy stage. Manual manipulation of the ultrasound probe would provide a more optimal visualization of the biopsy target and the biopsy needle in the same image. In another embodiment, the ultrasound probe may be electronically steered or remotely operated during the pre-biopsy stage and the biopsy stage, electronically steered during the pre-biopsy stage and manually manipulated in the biopsy stage, or manually manipulated during both the pre-biopsy stage and the biopsy stage.

In step 510, three-dimensional ultrasound images of the patient's breast are acquired in real-time. In step 512, the four-dimensional ultrasound images are used to locate the same endogenous fiducial markers identified in step 504. In step 514, the patient's current respiratory state is determined using the positional or spatial information of the endogenous fiducial markers in the ultrasound images. In step 516, the index or table of the previously determined respiratory states and their corresponding MR images is accessed, and the MR images associated with the patient's current respiratory state are retrieved. In step 518, a non-rigid body transformation is performed on the retrieved MR images of step 516. The non-rigid body transformation matches the positional state of the patient's breast during the pre-biopsy stage of the procedure with the current positional state of the patient's breast. For example, the breast outlines or the endogenous fiducial markers in the MR images and the ultrasound images are matched. Thus, the MR images are deformed to fit the ultrasound images.

This transformation of the MR images provides an accurate representation of the shape and position of the patient's breast during the biopsy procedure. The non-rigid body transformation of the MR images may be conducted at any time prior to the insertion of the biopsy needle into the patient for each set of MR images corresponding to the determined respiratory states during the pre-biopsy stage of the procedure. This provides an accurate map of the position of the patient's breast and tissues within the patient's breast (e.g., the suspect lesion, arteries, veins, fat layers, and muscle layers). If the position of the patient's breast changes during the biopsy procedure (e.g., during needle insertion), the non-rigid body transformation may be reapplied to each set of MR images to provide accurate, updated images with minimal computational overhead.

The respiratory state matching steps 512 to 516 and the deformable registration step 518 may be represented by a single mathematical transfer function or separate mathematical transformation functions. For example, the mathematical transformation functions may represent a mapping of one respiratory state to another, one positional state of a deformable anatomical structure (e.g., the breast) to another positional state, or a combination of both. A person of ordinary skill in the art should recognize that the mathematical transformation function may be any suitable geometric operation utilized with the observed anatomical markers in the ultrasound and MR images.

In step 520, the transformed MR images may be displayed to provide an accurate, real-time representation of the position of the suspect lesion and the surrounding anatomical details of the breast to guide the biopsy needle. However, a signal, such as a red dot, may be displayed if no MR image is available that corresponds to the current respiratory state of the patient.

In step 522, the position of the biopsy needle may be derived from the real-time ultrasound images or the external positional markers on the biopsy needle holder. For example, the external positional markers may include infrared sensors, magnetoresistance sensors, or other suitable means. The position of the biopsy needle may then be overlaid onto the displayed MR images. To ensure accuracy of the overlay, the MR image frame-of-reference and the biopsy needle frame of reference may be calibrated. For example, infrared sensors on the biopsy needle may be used to identify the position of the biopsy needle tip and the orientation and trajectory of the biopsy needle. Simple calibration of the position and angle of the biopsy needle tip is performed to align and register the MR image frame-of-reference to the biopsy needle frame of reference.

In step 524, the completion of the biopsy is determined. If the biopsy of the suspect lesion is determined to have been successfully completed, the procedure terminates. However, if the biopsy is determined to be incomplete, the imaging and guidance procedure may continue to be performed until the biopsy of the suspect lesion is determined to have been successfully completed.

While the embodiments described hereinabove perform the procedure with the patient in the supine position, a person skilled in the art should recognize that the procedure is not limited as such by the patient's position. The procedure may be performed on the patient in the prone position. For example, the procedure may require the use of a supporting structure to allow the breast of the patient to be suspended while the patient is in the prone position. Additionally, a corresponding MRI receiver coil customized for the breast may be necessary.

Technical effects of the disclosure include providing virtual real-time MRI-guidance for a breast biopsy outside of a conventional MRI scanner. This allows for active visualization of the biopsy needle progression or verification of the biopsy site of the patient outside of the MRI scanner. The biopsy and imaging procedure permits the patient to be in the more comfortable supine position instead of the prone position. Additionally, the procedure may be performed without the need for breast compression or the use of plates to guide the biopsy needle.

This written description uses examples, including the best mode, to enable any person skilled in the art to practice the invention, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for providing real-time image guidance for a biopsy, comprising:
    acquiring a plurality of MR images of an anatomical region of a patient;
    acquiring a plurality of pre-biopsy ultrasound images of the anatomical region, wherein the MR images and the pre-biopsy ultrasound images are acquired simultaneously;
    determining, by a processor, a plurality of respiratory states of the patient from the pre-biopsy ultrasound images, wherein the plurality of respiratory states include inhalation and exhalation, and a respective respiratory state is associated with one or more MR images;
    indexing, by the processor, the MR images with their corresponding respective respiratory state; and
    storing the MR images with their corresponding respective respiratory state.

2. The method of claim 1, comprising identifying an endogenous fiducial marker in the pre-biopsy ultrasound images.

3. The method of claim 2, wherein determining the plurality of respiratory states of the patient from the pre-biopsy ultrasound images is based on a positional change or change in shape of the anatomical region with respect to the identified endogenous fiducial marker.

4. The method of claim 1, wherein the anatomical region of the patient includes a breast of the patient.

5. The method of claim 4, wherein the MR images and the pre-biopsy ultrasound images are acquired without breast compression.

6. The method of claim 1, wherein the plurality of respiratory states further include at least one of short-breath holds and irregular breaths.

7. The method of claim 1, wherein the respective respiratory state is associated with one or more MR images by substantially aligning the MR images with the pre-biopsy ultrasound images along a time direction.

8. The method of claim 1, wherein the patient is in a supine position.

9. A method for providing real-time image guidance for a biopsy, comprising:
    acquiring a plurality of biopsy ultrasound images of an anatomical region of a patient;
    determining, by a processor, a biopsy respiratory state from the biopsy ultrasound images, wherein the biopsy respiratory state is identified as one of a plurality of respiratory states of the patient associated with one or more stored MR images of the patient, wherein the plurality of respiratory states include inhalation and exhalation, the one or more stored MR images were acquired simultaneously with pre-biopsy ultrasound images of the anatomical region;
    retrieving, by the processor, the stored MR images that correspond to the identified biopsy respiratory state; and
    displaying, by the processor, the stored MR images that correspond to the identified biopsy respiratory state.

10. The method of claim 9, comprising deforming the stored MR images to substantially match the structure of the anatomical region of the patient during the identified biopsy respiratory state.

11. The method of claim 9, comprising displaying a position of a biopsy needle on the displayed MR images.

12. The method of claim 11, wherein the position of the biopsy needle is displayed by identifying a position or an orientation of the biopsy needle using infrared sensors or magnetoresistance sensors.

13. An interventional guidance system, comprising:
an ultrasound imaging system configured to acquire pre-biopsy ultrasound images and biopsy ultrasound images of an anatomical region of the patient; and
a processor configured to:
   determine a plurality of respiratory states of the patient from the pre-biopsy ultrasound images; wherein the plurality of respiratory states include inhalation and exhalation;
   associate the plurality of respiratory states with one or more MR images, wherein the one or more MR images were acquired simultaneously with the pre-biopsy ultrasound images;
   index the MR images with their corresponding respiratory states;
   determine a biopsy respiratory state from the biopsy ultrasound images, wherein the biopsy respiratory state is identified as one of the plurality of respiratory states associated with the one or more MR images; and
   display the MR images that correspond to the identified biopsy respiratory state.

14. The interventional guidance system of claim 13, wherein the interventional guidance system is in communication with an MRI scanner configured to acquire the one or more MR images of the anatomical region of the patient.

15. The interventional guidance system of claim 13, comprising a biopsy needle sensor, wherein the processor is configured to display a position of the biopsy needle on the displayed MR images.

16. The interventional guidance system of claim 15, wherein the biopsy needle sensor includes infrared sensors or magnetoresistance sensors for tracking a position or an orientation of the biopsy needle.

17. The interventional guidance system of claim 13, wherein the anatomical region of the patient includes a breast of the patient and the MR images, the pre-biopsy ultrasound images, and the biopsy ultrasound images are acquired without breast compression.

18. The interventional guidance system of claim 13, wherein the ultrasound imaging system includes an MR-compatible ultrasound probe.

19. The interventional guidance system of claim 13, wherein the processor is configured to deform the MR images to fit the structure of the anatomical region of the patient during the identified biopsy respiratory state.

20. The interventional guidance system of claim 13, wherein the processor is configured to identify an endogenous fiducial marker from the pre-biopsy ultrasound images and biopsy ultrasound images.

* * * * *